(12) United States Patent
Liu

(10) Patent No.: US 7,652,755 B2
(45) Date of Patent: Jan. 26, 2010

(54) APPARATUS AND METHOD FOR COLOR MEASUREMENT AND COLOR GRADING OF DIAMONDS, GEMSTONES AND THE LIKE

(76) Inventor: Yan Liu, 1460 Rockhaven St., Monterey Park, CA (US) 91745

( * ) Notice: Subject to any disclaimer, the term of this patent is extended or adjusted under 35 U.S.C. 154(b) by 411 days.

(21) Appl. No.: 11/678,564

(22) Filed: Feb. 23, 2007

(65) Prior Publication Data

US 2008/0204705 A1 Aug. 28, 2008

(51) Int. Cl.
  *G01N 21/00* (2006.01)
  *G01J 1/04* (2006.01)
(52) U.S. Cl. .................... 356/30; 356/236; 250/228
(58) Field of Classification Search .............. 356/30, 356/406, 236; 250/228
See application file for complete search history.

(56) References Cited

U.S. PATENT DOCUMENTS

| | | | | |
|---|---|---|---|---|
| 4,120,582 A | * | 10/1978 | De Vries et al. | 356/73 |
| 5,615,005 A | * | 3/1997 | Valente et al. | 356/30 |
| 6,040,904 A | * | 3/2000 | Fallet et al. | 356/236 |
| 6,346,713 B1 | * | 2/2002 | Van Valkenburg | 250/559.45 |

* cited by examiner

*Primary Examiner*—Tarifur Chowdhury
*Assistant Examiner*—Tara S Pajoohi
(74) *Attorney, Agent, or Firm*—Charles C. H. Wu; Wu & Cheung, LLP

(57) ABSTRACT

The present invention discloses an apparatus that comprises a spectrometer, and computer and a dual integrating sphere measurement arrangement comprising a measurement integrating sphere, a sample integrating sphere, a sample platform, a filter, a lens system, a baffle and a light source. The sample integrating sphere encloses a sample to provide a constant environment for simulating the visual color grading environment. The computer controls the spectrometer and provides measurement parameters calculated from physical parameters of the measured sample, including, but not limited to, shape, dimensions, refractive index, intensity of fluorescence and cut grade. The computer then calculates spectral reflectance and colorimetric data, and determines an average color grade by checking a look-up-table that represents the relationship between the CIELAB coordinate and the average color grade. The computer also determines a true color grade based upon the average color grade and the physical parameters, using mathematical analytic algorithms.

13 Claims, 2 Drawing Sheets

1. Measurement integrating sphere; 2. Sample integrating sphere; 3. Sample platform;
4. Measurement window; 5. Measurement window filter; 6. Lens system; 7. Light trap; 8.Baffle;
9. Light source; 10. Sample; 11. Spectrometer; and 12. Computer.

APPARATUS AND METHOD FOR COLOR MEASUREMENT AND COLOR GRADING OF DIAMONDS, GEMSTONES AND THE LIKE

BACKGROUND OF THE INVENTION

1. Field of the Invention

The present invention relates to an apparatus and method for color measurement and color grading of diamonds, gemstones and the like, and more particularly, an apparatus and method for measuring the spectral reflectance, for calculating the calorimetric data, and for determining the average color grade and the true color grade of a sample.

2. Description of the Related Art

Although color measurement is constant and accurate in general, color measurement and color grading of diamonds, gemstones and the like is difficult and often inaccurate for gemological researchers and jewelers because visual color grading involves many human factors and because faceted diamonds and gemstones are usually in irregular shapes and sizes. At best, all of the previous inventions and commercial instruments for color measurement of gemstones can only measure particular colors without determining the true meaning of the color.

An early invention for color grading of colorless to light yellow diamonds was disclosed by Shipley in U.S. Pat. No. 2,960,909. This invention passes a concentrated light beam through a diamond and onto a photocell connected to a microammeter. Based upon the ratio between a blue beam and a minus-blue beam, a microammeter determines the color (grade) of the measured diamond.

Eickhorst (U.S. Pat. No. 3,794,424) uses a light conductor to directly illuminate the table of a gemstone and an optical transmitter to collect reflect light for the photocell to measure. Makabe (U.S. Pat. No. 4,482,245) describes an apparatus for measuring diamond color with an integrating sphere. The integrating sphere provides uniform light for illuminating the diamond and collects all reflect light. Okazaki (U.S. Pat. No. 4,508,449) improves the previous inventions and discloses an apparatus comprising a monochromator and an integrating sphere with a diamond holder. The light beam directly illuminates the diamond inside the holder, and the integrating sphere collects the reflect light for the monochromator to measure. This device uses a visible spectral curve to determine the color grade. However, each of these inventions had a low color measurement accuracy below the requirement of the gem trade.

Hohberg et al. (U.S. Pat. No. 5,164,586) discloses an arrangement for color measurement of gemstones. This arrangement includes an integrating sphere and a dual channel spectrometer. The integrating sphere provides a uniform lighting for the gemstone, and transmitted light is measured. However, because transmitted light from pavilion to table is significantly different from the transmitted light through the side and the reflected light of faceted diamonds, this invention is neither practical nor useful.

Valente et al. (U.S. Pat. No. 5,615,005) discloses a gemstone evaluation system, with an integrating sphere, a band pass filter and a detector array. This system obtains the spectral reflectance of a complete image, and can provide a color image, a spectral measurement and calorimetric data for each individual pixel of the image. However, a band pass filter is not accurate or stable enough for the color measurement of gemstones. Practically, the system is also not accurate enough for color grading purposes.

De Jong and Geurts (U.S. Pat. No. 7,004,624) disclose an apparatus for diamond color measurement and analysis. This apparatus simulates the human visual color grading method and environment for the D-Z color grading of diamonds. However, the detector of the apparatus is only a simple collimator without any of the functions of a human visual system. Thus, this apparatus has no practical application.

Furthermore, two inventions previously disclosed by applicant are considered relevant to date by applicant, but do not anticipate nor teach the present invention. First, Liu (U.S. PTO No. 11/129,703) discloses optical filters for a CIE daylight simulator. The optical filters consist of two or more layers of colored glasses designed by optimization algorithms. When combined with a high color temperature incandescent, the filters can simulate a CIE standard daylight illuminant with a metamerism index B or better in the visible wavelength range. The calorimetric quality of the CIE daylight simulators at different color temperatures meets the CIE, ISO and ASTM standards for calorimetric and critical applications. In addition, Liu (U.S. PTO No. 11/322,431) also discloses a method and system for visual color grading of gemstones. The system can accurately generate a reference color to match the color of a gemstone under a standard viewing environment. Based on the matched color, the gemstone is assigned a color grade by a look-up-table representing the relationship between the color grades and the CIELAB coordinates.

Therefore, there remains a need for an apparatus capable of accurate color measurement of gemstones, diamonds and the like, and more importantly, of precise color grading of same.

SUMMARY OF THE INVENTION

Accordingly, one object of the present invention is to provide a color measurement apparatus and method that can accurately measure the color of gemstones, and more importantly, can determine color grades that are consistent with the grades obtained by visual color grading methods.

A second object of the invention is to provide a color measurement apparatus that can use said method to measure the color of faceted gemstones and to determine the color grades of same.

A third object of the invention is to provide a color measurement apparatus that can use said method to measure the color of faceted colored diamonds and to determine the color grades of same.

A fourth object of the invention is to provide a color measurement apparatus that can use said method to measure the color of colorless to light yellow diamonds, and to determine the color grades of same in the D-Z scale.

A fifth object of the invention is to provide a color measurement apparatus that can use said method to measure the color of rough gemstones, diamonds, minerals and the like and to determine the colors of same.

A sixth object of the invention is to provide a color measurement apparatus that is practical and inexpensive to manufacture.

To achieve these and other advantages and in accordance with the purpose of the invention, as embodied and broadly described herein, the invention provides an apparatus and method for measuring the color of gemstones, diamonds and like and determining the color grades accordingly. The method includes steps of inputting physical parameters, calculating the measurement parameters, measuring the spectral reflectance, calculating calorimetric data based on the spectral reflectance, determining the average color grade by checking the look-up-table, and determining the true color grade by using a mathematics method involving the average color grade and the physical parameters.

To implement the method, the invention provides an apparatus comprising of a spectrometer, a computer, and a dual integrating sphere measurement arrangement comprising a measurement integrating sphere, a sample integrating sphere, a measurement platform, a measurement window, a measurement window filter, a light source, a lens system, a light trap and a baffle. The measurement window filter converts the spectral power distribution of the light source in order to simulate the spectral power distribution of a CIE daylight illuminant. The measurement integrating sphere integrates the light from the light source and provides diffused light to illuminate the sample uniformly. The lens system in the measurement integrating sphere receives the reflected light from the sample, focuses the light into a fiber optic cable, and sends the light to the spectrometer through the fiber optic cable. The computer calculates the calorimetric data and determines the average color grade and the true color grade. The apparatus can measure the color of faceted and rough gemstones, diamonds and the like in any shape or size, and can accurately determine the average color grade and the true color grade of same.

The present invention utilizes a novel three-step procedure for calibrating the apparatus. The three-step calibration procedure includes white calibration, black calibration and an additional dual integrating spheres calibration.

DESCRIPTION OF THE PREFERRED EMBODIMENTS

Figure 1:
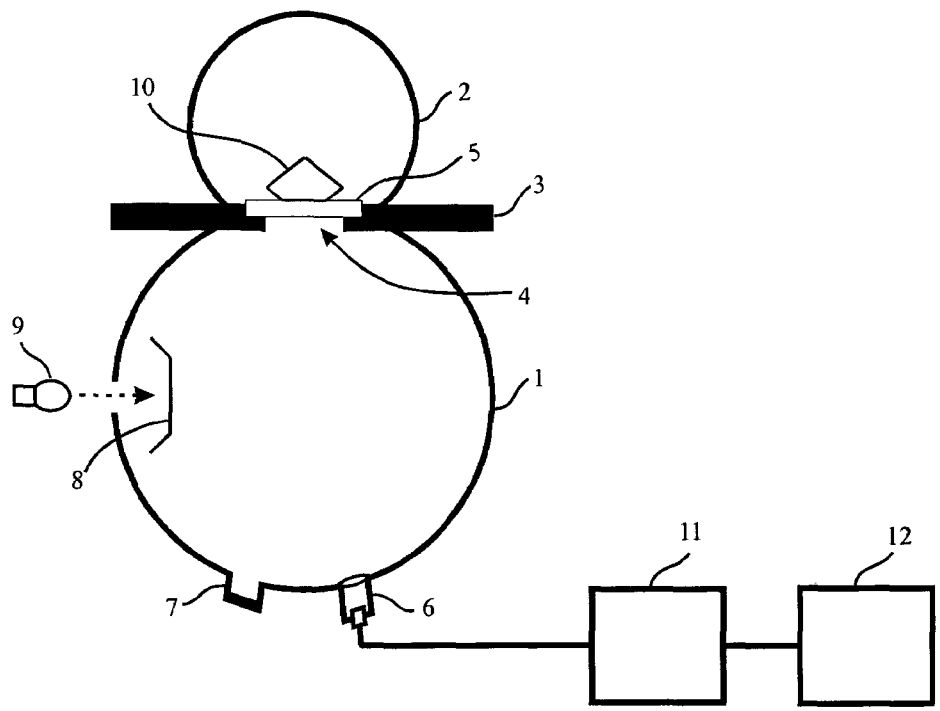
FIG. 1 is a schematic depicting an apparatus of the present invention with a computer, a spectrometer and the dual integrating sphere measurement arrangement.

FIG. 1 shows an apparatus according to an embodiment of the present invention for color measurement and color grading of gemstones, diamonds and the like. The apparatus includes a computer 12, a spectrometer 11 and the dual integrating sphere measurement arrangement comprising a measurement integrating sphere 1, a sample integrating sphere 2, a sample platform 3, a measurement window 4, a measurement window filter 5, a lens system 6, a light trap 7, a baffle 8, and a light source 9.

The measurement integrating sphere 1 and the sample integrating sphere 2 are connected together by the sample platform 3. In the middle of the sample platform 3, there is a round hole called the measurement window 4. The measurement window filter 5 is set in the middle of the platform 3, and the measurement window is in the middle of the measurement window filter. The sample 10, usually a faceted gemstone, a faceted diamond or the like, is placed table-down on the measurement window filter 5 inside the sample integrating sphere 2.

The sample integrating sphere 2 is on the top of the measurement integrating sphere 1 as illustrated in FIG. 1. The inside walls of the measurement integrating sphere 1 and the sample integrating sphere 2 are coated with a high reflectance materials, such as barium sulphate ($Ba_2SO_4$) or polytetrafluoroethylene (PTFE). The sample integrating sphere 2 can be removed from the apparatus in order to accommodate the sample 10 on the center of the measurement window filter 5 for measurement. The sample is placed at a table-down position in the center of the measurement window filter 4. The sample is held by gravity, so no sample holder accessory is necessary.

The total area of the measurement window 4, the output port of the lens system 6, the light trap 7 and the light port for the light source 9 shall be less than 10% of the total internal sphere area of the measurement integrating sphere 1. The open area of the sample integrating sphere 2 is equal to or larger than that of the measurement window filter 4.

The lens system 6, the light trap 7, the baffle 8, and the light source 9 are attached to the measurement integrating sphere 1. The measurement integrating sphere 1 provides diffused uniform illumination on the sample, collects the spectral reflectance light from the sample 10, and transmits the collected spectral reflectance light from the sample 10 to the spectrometer 11 by the lens system 6 through a fiber optic cable. The light source 9 emits light with a continuous spectral power distribution in the visible wavelength range in order to illuminate the baffle 8, which baffle 8 is inside the measurement integrating sphere 1. The baffle 8 diffusely reflects the light to the internal wall of measurement integrating sphere 1 and blocks any light that may be directly incident into the lens system 6 and the sample 10. The measurement integrating sphere 1 diffuses the light from the light source 9 to uniformly illuminate the sample 10 through the sample window 4 and the sample window filter 5, and then collects the reflected light from the sample 10.

The measurement window filter 5 changes the spectral power distribution of the light source 9 to a spectral power distribution required for illuminating the sample 10 for color grading purposes. A more specific spectral power distribution required for illuminating a gemstone for color grading of gemstones is a Commission Internationale de L'eclairage (hereinafter CIE) standard illuminant D65. According to the CIE, International Standard Organization (hereinafter ISO) and American Society for Testing and Materials (hereinafter ASTM) standards, the metamerism index of the D65 daylight simulator must be B or better for calorimetric purposes and critical applications.

To meet the daylight standards, Liu (U.S. PTO No. 11/129, 703) discloses several optic filters for simulating the CIE standard daylight illuminant with high color temperature incandescent lamps. The optic filter consists of two or more colored glass layers and combines with a high temperature incandescent lamp to simulate the CIE daylight illuminator with a metamerism index B or better in the visible wavelength range. Accordingly, the measurement window filter 5 is one of said filters disclosed by Liu. The thickness of each colored glass layer of the filter 5 shall be one-half of the thickness required for simulating the CIE standard daylight illuminant D65, because the measurement light passes through the filter 5 twice: first, the light passes through the filter 5 to illuminating the sample; then, the reflected light from the sample passes through the filter 5 again to the lens system 6. For a less critical application, the filter 5 is a color temperature conversion filter for increasing color temperature, such as a Schott FG5 or a Hoya LB80. If the end user is not considering fluorescence and color change of the measured gemstone, the filter 5 can be a longpass filter with a short edge wavelength at 400 nm or shorter.

The lens system 6 is installed in a fiber optic sample port of the measurement integrating sphere 1. The view field of the lens system 6 is restricted to the sample window with a divergence of about 2 degrees. The sample can be viewed at an angle between 1 degree to 25 degrees from normal to the measurement window; in the preferred embodiment, the sample is viewed at an angle of 8 degrees from the normal to the measurement window 4. The light trap 7 is opposite the lens system 6 at an angle of 8 degree from the normal to the measurement window 4. The light trap 7 absorbs all incident light, so as to eliminate any contribution of the surface reflection to the spectral measurement performed by the spectrometer 11. The spectral measurement with the arrangement of the lens system 6 and the light trap 7 is intended to exclude specular reflectance from the surface of the measurement window filter 5 and the sample 10. The illuminating and viewing geometry for the dual integrating sphere measurement arrangement is diffuse illuminant and 8° viewing with the specular component excluded plus diffuse white background provided by the sample integrating sphere, abbreviation d/8:e+d.

The spectrometer 11 receives spectral reflectance light from the lens system 6, separates the light into a spectrum, and converts the spectral intensities into digital accounts versus wavelength $\lambda$ in the visible wavelength range.

According to another aspect of the invention, the spectrometer 11 is calibrated by a novel three-step calibration method including white calibration, black calibration and an extra integrating sphere calibration. The white calibration is to measure a standard white tile on the measurement window filter 5 and to save the measured spectral digital counts as the white calibration file $W(\lambda)$. The black calibration is to measure a standard black tile and save the measured spectral digital counts as the black calibration file $B(\lambda)$. For taking the white and black calibrations, the measurement integrating sphere 2 is not required to be closed on the measurement platform 3. The integrating sphere calibration is to calibrate the dual integrating sphere arrangement and save the measured digital counts as the integrating sphere calibration file $IS(\lambda)$. When taking the integrating sphere calibration, the measurement integrating sphere 2 is closed on the measurement platform 3, and there is no object on the measurement window filter 5.

The computer 12 determines the spectral measurement parameters, controls the spectrometer for spectral measurement, calculates the calorimetric data, and determines the average color grade and the true color grade.

Figure 2:
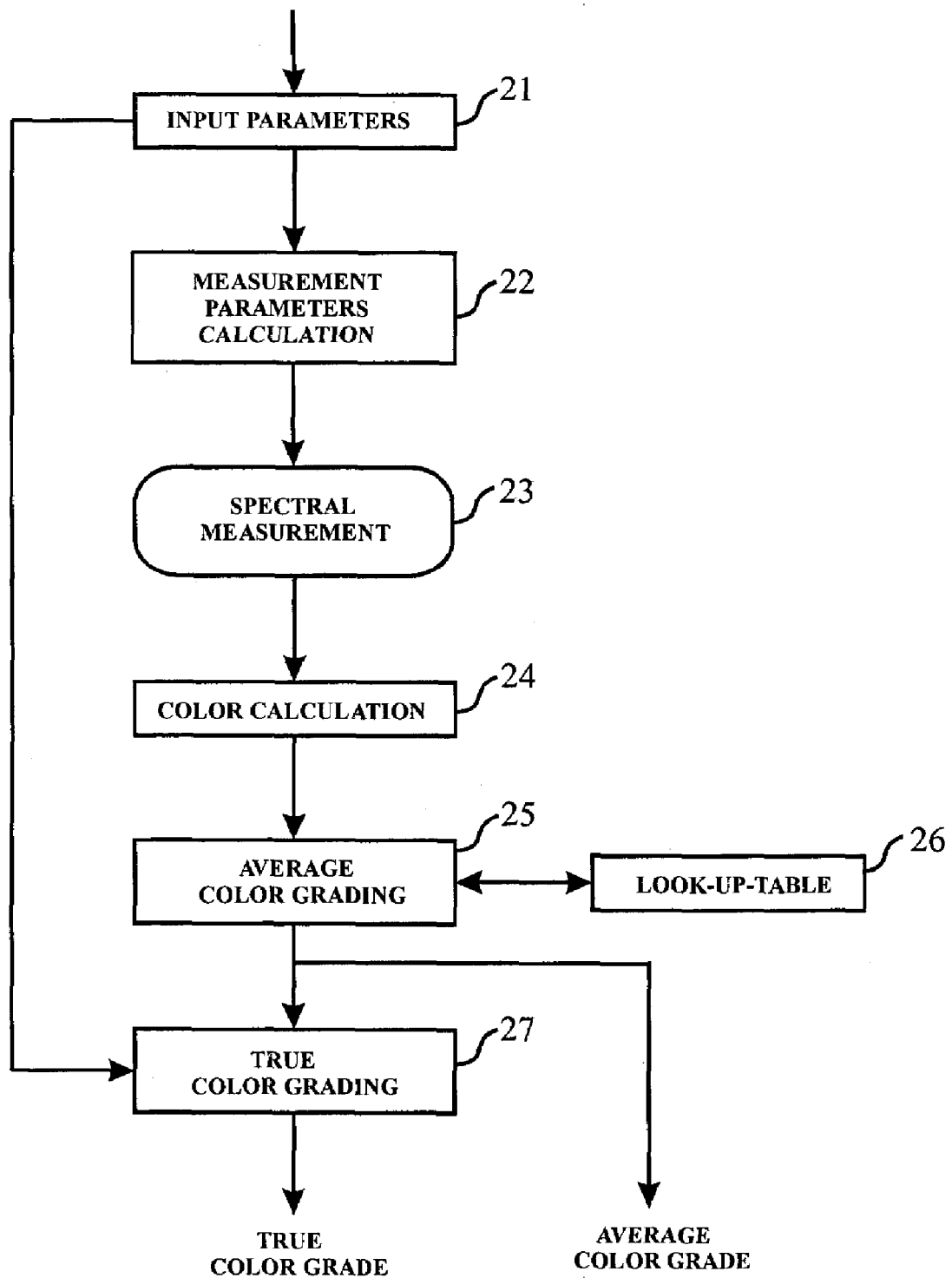
FIG. 2 is a flowchart depicting the method of color measurement and color grading.

With reference to FIG. 2, a flowchart depicts the method of the present invention. The method includes the steps of the input of physical parameters 21, measurement parameter calculation 22, spectral measurement 23, color calculation 24, average color grading 25 by checking a look-up-table 26, and true color grading 27.

The first step of the method is to input physical parameters 21 into the computer 12. The parameters include the sample's 10 shape, length, width, depth, refractive index, intensity of fluorescence and cut grade. Faceted gemstones can be in any shape, and it is impossible to list all of the shapes for the input 21. As an approximate approach, the input step 21 of the preferred embodiment only includes the most popular shapes, such as, but not limited to, round, oval, rectangle, marquise, and heart. Other shapes shall be substituted by the listed shapes with the most similar shapes. The shape of "princess cut," for example, shall be substituted by the rectangle shape.

Length, width and depth are measured in units of millimeters. The refractive index of a gemstone can be measured by a refractometer or other physics methods. The refractive index can also be obtained by checking references, such as books and articles.

According to the preferred embodiment, the cut grade is arbitrarily quantified in a scale from 0 to 100 as an input parameter. On the cut grade scale, 100 represents the perfect cut grade, which refers to a cut where all incoming light will be totally reflected back through the table; 90-99 represents the cut grade of excellent; 80-89 represents the cut grade of very good; 70-79 represents the cut grade of good; 60-69 represents the cut grade of fair; 1-59 represents the cut grade of poor; and 0 represents rough gemstones without faceting and polishing. The higher the cut grade of a gemstone, the better the true color grade because there is more internal reflection. When the cut grade is 0 for a rough gemstone, its true color grade is the same as its average color grade. For a gemstone with two parallel surfaces, its cut grade is also assigned as 0, and again its true color grade is the same as its average color grade.

According to the preferred embodiment, the intensity of fluorescence is arbitrarily quantified in a scale from 0 to 100 as an input parameter. On the fluorescence intensity scale, 0 represents inert, which means no fluorescence; larger then 0 to 10 represents faint; 10 to 30 represents weak; 30 to 50 represents medium; 50 to 70 represents strong; 70 to 90 represent very strong; and 90 to 100 represents extreme. The higher the intensity of fluorescence is, the more intense the fluorescence is. The fluorescence includes that caused by both ultraviolet and visible light.

In the step of measurement parameters calculation 22, the parameters for controlling the spectrometer 11 are calculated by mathematical algorithms using the physical parameters inputted in step 21. The mathematic algorithms are one or more mathematic methods including, but not limited to, complex numerical function, matrix transfer, finite element analysis, numerical analysis, artificial neural network, optimization, fuzzy logic, regression, possibility, and statistics. The calculated measurement parameters include, but are not limited to, integration time, samples to average, bandwidth, width of slit, boxcar width, and the voltage of the detector. In said step 22, the parameters for calculating the spectral reflectance are also calculated.

The measurement parameters calculated in the step 22 are sent to the spectrometer 11 for the spectral measurement 23. The spectrometer 11 uses the measurement parameters to set its measurement condition, and then to measure the spectral reflectance of the sample 10 on the measurement window filter 5 inside the sample integrating sphere 2. The spectrometer 11 outputs a digital count file $S(\lambda)$ for the spectral reflectance of the sample 10 to the computer 12 to calculate the spectral reflectance.

According to another aspect of the invention, two parameters called black calibration correction $\alpha$ and measurement integrating sphere correction $\kappa$ are introduced for calculating the spectral reflectance of the sample 10. Both the black calibration correction $\alpha$ and the measurement integrating sphere correction $\kappa$ are the function of the input parameters 21. As mentioned hereinabove, both the black calibration correction $\alpha$ and the measurement integrating sphere correction $\kappa$ are calculated in the step of measurement parameters calculation 22.

The spectral reflectance of the sample is calculated by the equation:

$$R(\lambda) = \frac{S(\lambda) - \alpha B(\lambda) - \kappa IS(\lambda)}{W(\lambda) - B(\lambda)} \qquad \text{(Equation 1)}$$

where $\lambda$ is wavelength in nanometers, $R(\lambda)$ is the spectral reflectance of the sample 10, $S(\lambda)$ is the measured digital counts of the sample 10, $W(\lambda)$ is the digital counts of the white calibration, $B(\lambda)$ is the digital counts of the black calibration, $IS(\lambda)$ is the digital counts of the integrating sphere calibration, $\alpha$ is the black calibration correction, and $\kappa$ is the integrating sphere calibration correction.

Because the white standard tile for the white calibration cannot be 100% reflectance in the measurement wavelength range and the black standard tile cannot be 0% reflectance, the white calibration W(λ) and black calibration B(λ) can be further corrected for a higher accuracy. Accordingly, considering the white standard tile correction and black standard tile correction, the Equation 1 is changed to:

$$R(\lambda) = \frac{S(\lambda) - \alpha C_2(\lambda)B(\lambda) - \kappa IS(\lambda)}{C_1(\lambda)W(\lambda) - C_2(\lambda)B(\lambda)} \quad \text{(Equation 2)}$$

where $C_1(\lambda)$ is the white standard tile spectral correction parameter and $C_2(\lambda)$ is the black standard tile spectral correction parameter. The spectral reflectance of the white and black standard tiles can trace to that of the white and black standards at the National Institute of Standards and Technology in Gaithersburg, Md. The white and black standard tile spectral correction parameters can be calculated by the known spectral reflectance of the white and black standard tiles.

The spectral reflectance R(λ) obtained from the Equation 2 is used for calculating the calorimetric data in the step of color calculation 24. In the preferred embodiment, the calculated calorimetric data include $L^*$, $a^*$, $b^*$, $C^*_{ab}$ and $h_{ab}$ in the CIELAB color space. $L^*$ is the lightness, $+a^*$ represent red color and $-a^*$ represents green color, $+b^*$ represents yellow color and $-b^*$ represents blue color, $C^*_{ab}$ is the chroma or the saturation and $h_{ab}$ is the hue angle.

The calorimetric data can also be expressed in other color spaces, including a CIELUV color space or a 1931 CIE color space. In a CIELUV color space, the calorimetric data includes $L^*$, $u^*$, $v^*$, saturation $S_{uv}$ and hue-angle $h_{uv}$. In a 1931 CIE color space, the calorimetric data includes x, y, and Y coordinates.

The CIELAB coordinates $L^*$, $a^*$ and $b^*$ are used in the next step of average color grading 25 to assign a color grade. The computer 12 checks the look-up-table to locate the color grade corresponding to the $L^*$, $a^*$ and $b^*$ coordinate of the sample. The look-up-table represents the relationship between the color grades and the CIELAB color coordinate ($L^*$, $a^*$, $b^*$). Each CIELAB color coordinate ($L^*$, $a^*$, $b^*$) corresponds to a color grade, but each color grade covers a large volume of color space. The color grade obtained in this step 25 is outputted as the average color grade. The average color grade is also sent to the next step of true color grading 27 to determine a true color grade.

According to another aspect of the invention, the preferred embodiment determines the true color grade from the average color grade and the input parameters 21. The true color refers to the "key color" defined by the Gemological Institute of America (hereinafter GIA) for the faceted colored gemstones, and refers to the "characteristic color" (also defined by GIA) for the colored diamonds.

The true color grade is determined by the average color grade and the physical parameters using the mathematics analyses and algorithms including, but not limited to, finite element analysis, numerical analysis, artificial neural network, optimization, fuzzy logic and regression. The true color grade corresponds to a visual color grading performed by human color graders under controlled illuminating and viewing geometries and under standard environments.

Other embodiments of the invention will appear to those skilled in the art from consideration of the specification and practice of the invention disclosed herein. It is intended that the specification and the description to be considered as exemplary only, with a true scope and spirit of the invention being indicated by the following claims.

What is claimed is:

1. A color measurement and color grading apparatus comprising:
   a measuring means for measuring the spectral reflectance of a sample;
   a dual integrating sphere measurement arrangement that is configured to house a sample, provide diffused uniform illumination on the sample, collect reflectance light from the sample, and transmit the reflectance light to the measuring means;
   a computer that is configured to calculate measurement parameters, control the measuring means; calculate colorimetric data, determine average color grade, and determine true color grade
   wherein said dual integrating sphere measurement arrangement is comprised of:
   a sample integrating sphere that is configured to provide a diffuse white measuring environment for a sample, which sample integrating sphere has a bottom, an internal area, and an open area;
   a measurement integrating sphere with at least one fiber optic sample port, a light port, an internal area, an open area, and a top;
   a sample platform connecting the measurement integrating sphere to the sample integrating sphere, which sample platform has an upper surface, a bottom surface, and a middle, and which sample platform contains a round hole called a measurement window;
   a measurement window filter, set on the sample platform, which measurement window filter is configured to accommodate a sample; a lens system attached to the measurement integrating sphere and configured to receive reflectance light from the sample;
   a light trap configured to eliminate specular reflection, and attached to the measurement integrating sphere;
   a light source configured to provide spectral power radiation in the visible wavelength range, attached to the measurement integrating sphere; and
   a baffle attached to the measurement integrating sphere and configured to block the light from the light source directly to the sample and said lens system.

2. The dual integrating sphere measurement arrangement according to claim 1 wherein the bottom of said sample integrating sphere is on the upper surface of said sample platform and the bottom surface of said platform is on the top of said measurement integrating sphere.

3. The dual integrating sphere measurement arrangement according to claim 1 wherein said sample integrating sphere can be taken off of the apparatus, a sample can be inserted or removed from the apparatus, and the sample integrating sphere can be placed back onto the apparatus.

4. The dual integrating sphere measurement arrangement according to claim 1 wherein the open area of said sample integrating sphere is equal to or larger than said measurement window filter and exceeds 1 percent of the internal area of the sample integrating sphere.

5. The dual integrating sphere measurement arrangement according to claim 1 wherein the total area of the measurement window, light trap, fiber optic sample port and light port of said measurement integrating sphere does not exceed 50 percent of the internal area of the measurement integrating sphere.

6. The dual integrating sphere measurement arrangement according to claim 1 wherein said measurement window filter is set in the middle of said sample platform.

7. The dual integrating sphere measurement arrangement according to claim 1 wherein said measurement window filter comprises one or more layers of materials capable of simulating CIE standard daylight illuminator in conjunction with said light source, said materials having been selected from the group consisting of colored glasses and optical thin films.

8. The dual integrating sphere measurement arrangement according to claim 1 wherein the view field of said lens system is restricted to said measurement window with a 1 to 25 degree viewing angle from normal to said measurement window.

9. The dual integrating sphere measurement arrangement according to claim 1 wherein the measurement integrating sphere is configured to integrate the light from said light source and provide diffuse illumination on the sample uniformly.

10. The dual integrating sphere measurement arrangement according to claim 1 wherein said sample integrating sphere is configured to accommodate the sample in the middle of said measurement window filter in a table-down position.

11. The apparatus according to claim 1, wherein said measuring means is calibrated by a white calibration using a standard white tile, a black calibration using a standard black tile; and an integrating sphere calibration without any foreign object inside the dual integrating sphere measurement arrangement.

12. The apparatus according to claim 1, wherein said measuring means is selected from the group consisting of a spectrometer, spectrophotometer, spectral imaging system, spectral graphic system and spectroradiometer.

13. The apparatus according to claim 1, wherein said measuring means is a colorimeter with R, G and B detectors.

* * * * *